(12) United States Patent
Yu et al.

(10) Patent No.: US 8,148,059 B2
(45) Date of Patent: Apr. 3, 2012

(54) METHOD OF DETECTING MALIGNANCY OF NASOPHARYNGEAL CARCINOMA AND A NASOPHARYNGEAL CARCINOMA MALIGNANCY BIOMARKER

(75) Inventors: Jau-Song Yu, Tao-Yuan (TW); Kai-Ping Chang, Taipei (TW)

(73) Assignee: Chang Gung University, Kwei-Shan Tao-Yuan (TW)

( * ) Notice: Subject to any disclaimer, the term of this patent is extended or adjusted under 35 U.S.C. 154(b) by 0 days.

(21) Appl. No.: 12/610,008

(22) Filed: Oct. 30, 2009

(65) Prior Publication Data

US 2011/0104657 A1    May 5, 2011

(51) Int. Cl.
*C12Q 1/70* (2006.01)
(52) U.S. Cl. .............................. 435/5; 435/345
(58) Field of Classification Search .................. None
See application file for complete search history.

(56) References Cited

OTHER PUBLICATIONS

Abiko et al, Archives of Oral Biology, 2003, vol. 48, 171-175.*
Chang et al., "Macrophage Inflammatory Protein-3α is a Novel Serum Marker for Nasopharyngeal Carcinoma Detection and Prediction of Treatment Outcomes" Nov. 1, 2008, p. 6979-p. 6987, Clin Cancer Res 2008.
Kleeff et al., "Detection and Localization of MIP-3/LARC/Exodus, a Macrophage Proinflammatory Chemokine, and its CCR6 Receptor in Human Pancreatic Cancer" p. 650-p. 657, Publication of the International Union Against Cancer Publication: 81, 1999 Wiley-Liss, Inc.
Bell et al., "In Breast Carcinoma Tissue, Immature Dendritic Cells Reside within the Tumor, whereas Mature Dendritic Cells Are Located in Peritumoral Areas" Nov. 15, 1999, p. 1417-1425, vol. 190, No. 10, The Rockefeller University Press.
Campbell et al., "Macrophage Inflammatory Protein-3 Promotes Pancreatic Cancer Cell Invasion" p. 96-p. 101, Journal of Surgical Research 123, (2005).
Yamauchi et al., "Increased serum levels of macrophage inflammatory protein-3 •in hepatocellular carcinoma: Relationship with clinical factors and prognostic importance during therapy" p. 601-605, 2003, International Journal of Molecular Medicine 11.
Myers et al., "Cancer of oral cavity," Cancer of the Head and Neck, 4th Edition, Philadelphia, PA: Saunders, 2003, Chapter 13, pp. 279-320.
Wei et al., "Cancer of the nasopharynx," Cancer of the Head and Heck, 4th Edition, Philadelphia, PA: Saunders, 2003, Chapter 11, pp. 229-250.

* cited by examiner

*Primary Examiner* — Ali R. Salimi
(74) *Attorney, Agent, or Firm* — Muncy, Geissler, Olds & Lowe, PLLC

(57) ABSTRACT

A method of detecting malignancy of nasopharyngeal carcinoma and a nasopharyngeal carcinoma malignancy biomarker are disclosed. Firstly, a specimen is obtained from a testee. Next, the specimen is tested for its MIP-3α expression level. Then, the MIP-3α expression level of the specimen is compared with that of a control. Finally, the malignancy of nasopharyngeal carcinoma is determined according to a relative MIP-3α expression level between the specimen and the control.

5 Claims, 17 Drawing Sheets

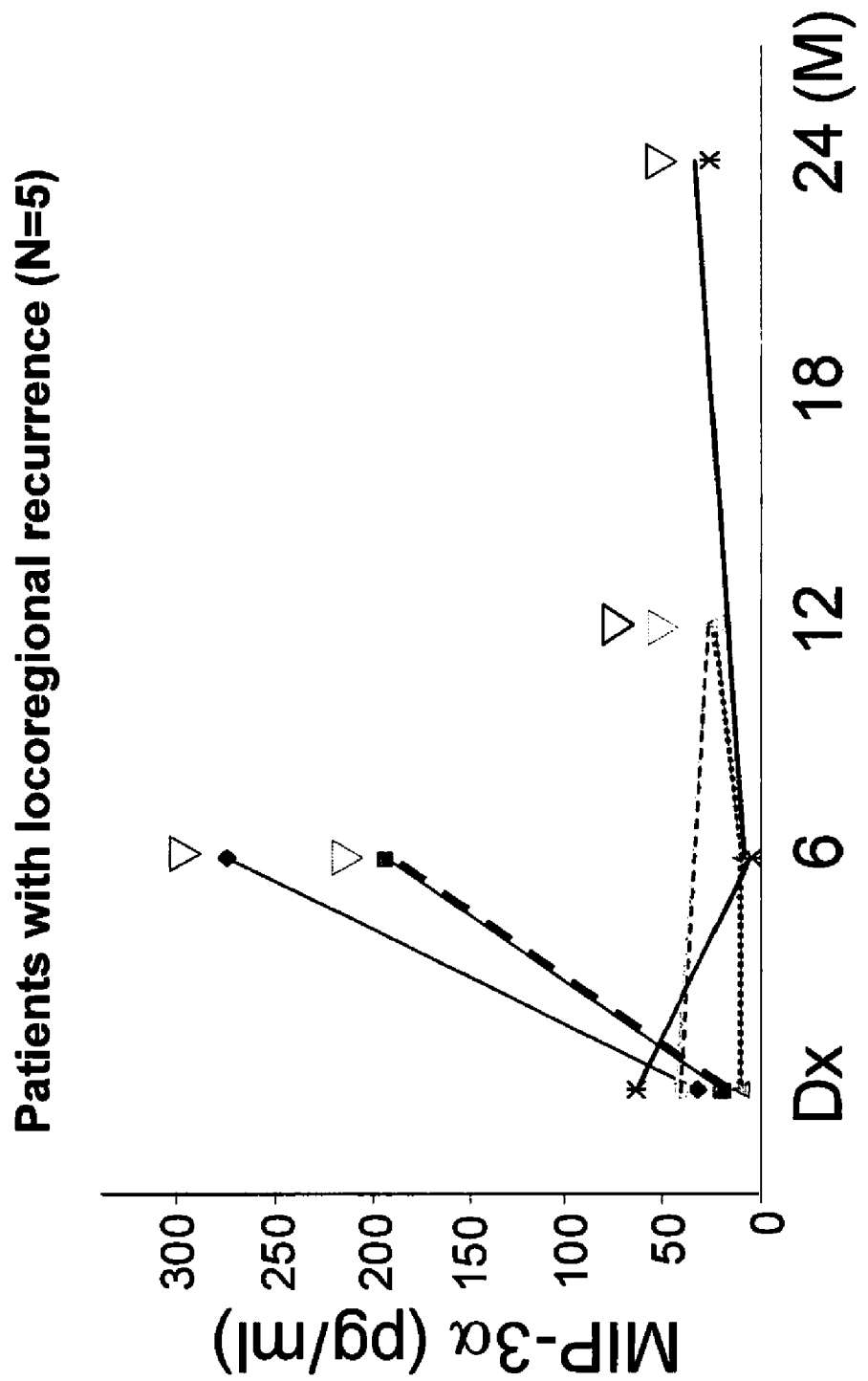

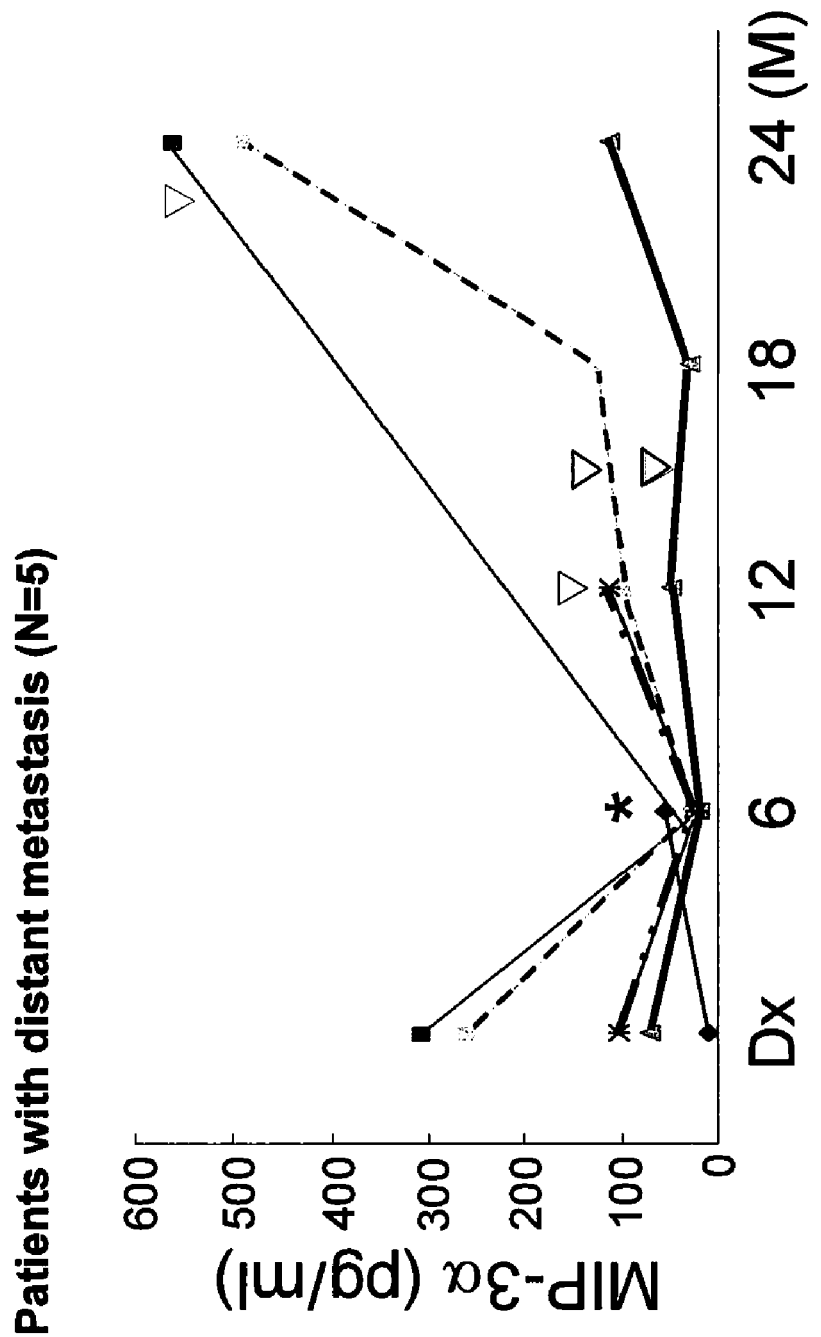

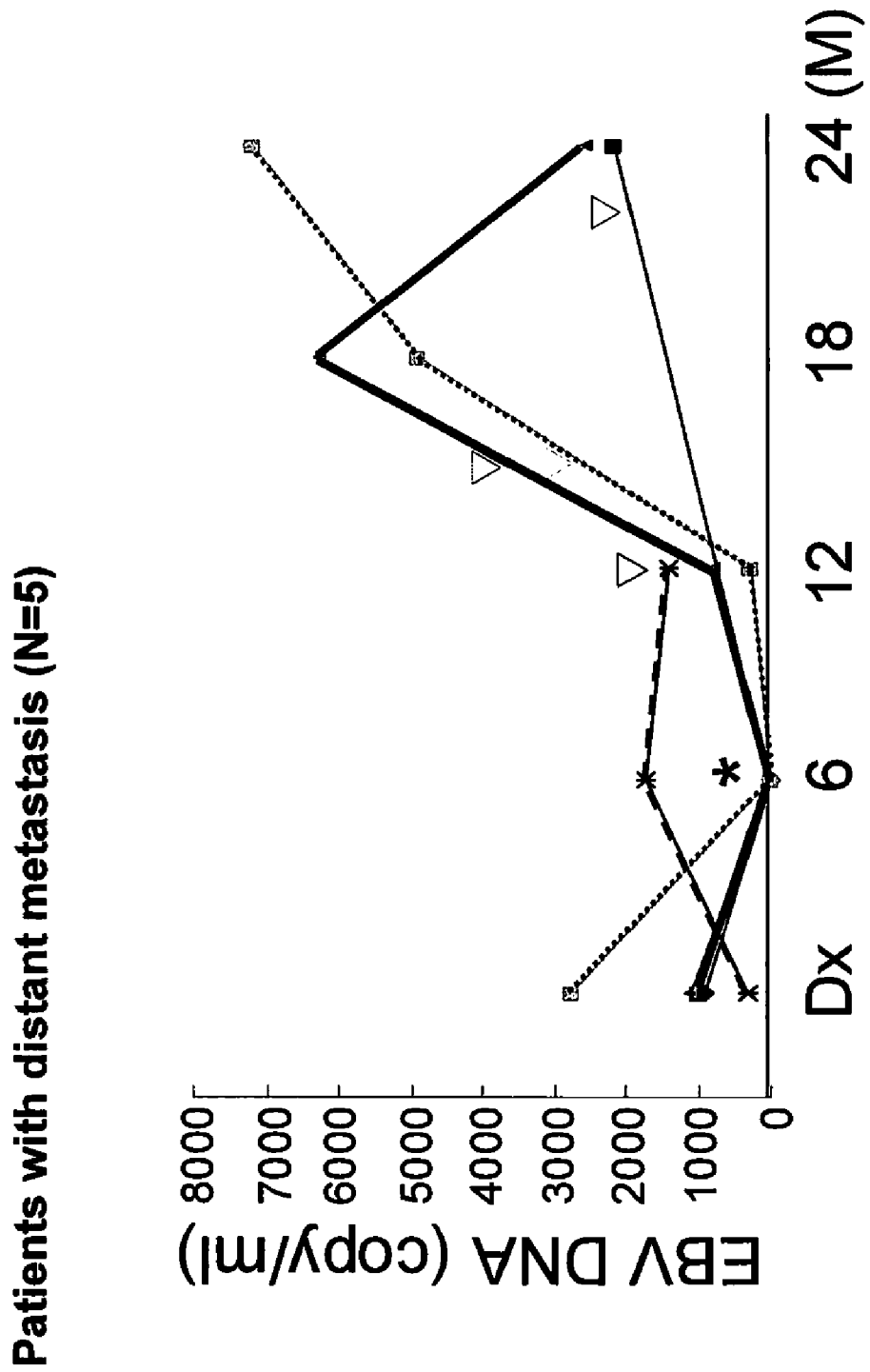

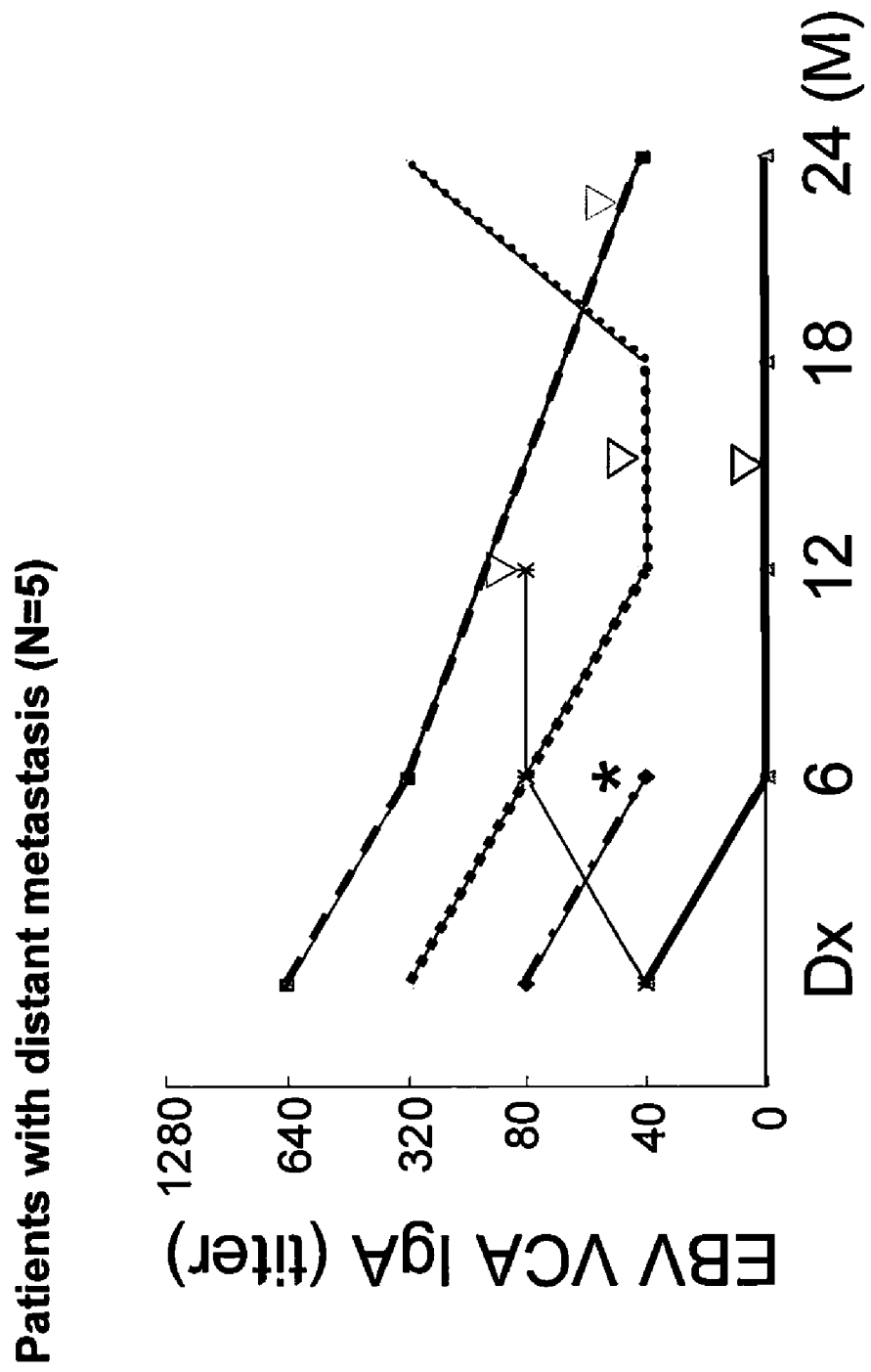

METHOD OF DETECTING MALIGNANCY OF NASOPHARYNGEAL CARCINOMA AND A NASOPHARYNGEAL CARCINOMA MALIGNANCY BIOMARKER

FIELD OF THE INVENTION

The present invention relates to a technology for testing nasopharyngeal carcinoma malignancy, and in particular to a macrophage inflammatory protein 3α (MIP-3α) biomarker for detecting the malignancy of nasopharyngeal carcinoma and a method thereof.

DESCRIPTION OF THE RELATED ART

Nasopharyngeal carcinoma (NPC) is a major head and neck cancer in Taiwan with a reported prevalence of 7-8/100,000 persons. The mean age of NPC patients is around 45 years old and the male to female ratio is approximately 2-3 to 1 [1,2]. Because NPC is an epithelial malignancy originating in the fossa of Rosenmuller and deep centrally inside the human skull, the symptoms and signs of NPC are usually insidious and vague. Patients usually seek medical consultations at more advanced stage due to some non-specific signs and symptoms at presentation including painless, enlarged cervical lymph nodes, nasal obstruction, epistaxis, diminished hearing, tinnitus, recurrent otitis media, cranial nerve dysfunction, sore throat and headache [3]. The difficulty of a thorough nasopharyngeal examination is also one of possible reasons accounting for late diagnoses [3].

Unique among all head and neck malignancies, radiotherapy is the mainstay treatment of NPC, with a 5-year actuarial survival of more than 70% and local control rate of more than 80% [4]. Although NPC is a radiosensitive tumor, radiotherapy still fail in a high percentage of NPC patients locoregionally. The reported incidence of local recurrence in NPC after initial radiotherapy has varied from 18% to 54% [5,6]. In order to improve the locoregional control and overall survival, concurrent chemoradiotherapy has gradually become the popular and standard treatment, especially for advanced stage diseases. With concurrent chemoradiotherapy, the five-year overall survival and disease-free survival for advanced NPC recently exceeded 70% [7,8].

Despite the improving outcome of concurrent chemoradiotherapy administration, some patients still unfortunately fail to respond locally in the nasopharynx. Recurrent NPC is a disease with a poor prognosis as re-irradiation has poor response rates and causes many severe complications [9,10]. Under such a circumstance, salvage surgery has been valued as a well-established and feasible treatment to avoid these grave outcomes and complications. The 10-year experience of salvage surgery for recurrent NPC was reported after radiation failure at the primary site. The actuarial 3-year survival and local control rate was 60% and 72.8%, respectively. Ten (83.3%) out of twelve patients with intracranial and skull base invasion achieved local control. There was no surgical mortality, and the morbidity rate was only 13.2% [11]. The results of this study revealed that the adequate exposure provided by the facial translocation approach with an integrate concept of skull base surgery and the collaboration of neurousurgeons could extend the surgical indications of salvage surgery for recurrent NPC in the primary site and resect many advanced lesions with acceptable mortality and morbidity.

Since EBV genomes are present in almost every NPC tumor cell, irrespective of histologic differentiation and geographical distribution [12-14], traditionally various EBV-derived/related factors have been used as NPC tumor markers. The EBV-specific viral capsid antigen (VCA), IgA, shows good sensitivity but has a high false-positive rate for primary screening, and poor specificity for discriminating NPC from other EBV-associated diseases in endemic areas [15, 16]. Cell-free EBV DNA has been shown to be a good indicator and prognosticator for NPC primary screening and overall survival, respectively [17-19]. However, because quantitative analysis of plasma/serum EBV DNA requires elaborate procedures and specialized equipment, this screening method is usually inaccessible to general practitioners in endemic areas and is therefore mostly used for post-treatment monitoring.

Although many patients with advanced NPC have a good probability of cure with concurrent chemoradiotherapy, tumor stage at initial presentation is still a major prognosticator of patient survival [20, 21]. Unfortunately, as mentioned above, most NPC patients in endemic areas present with advanced stages at diagnosis, owing to the insidious clinical course of NPC and the relatively inaccessible anatomical site of the nasopharynx. Traditionally, EBV-derived products were regarded as good biomarker for NPC detection and monitoring. However, although EBV VCA IgA and DNA load were two popular items used as NPC markers currently. Elevated EBV DNA load was found in other diseases (for example, lymphoproliferative disease) and normal individuals living in the endemic areas sometimes were high IgA VCA titers. These phenomena indicate that these EBV-derived markers are therefore not completely specific individually for NPC diagnostic. Searching for a panel screening to combine with EBV and non-EBV cellular markers might further provide a solution to raise the efficacy for NPC detection and treatment monitoring. Thus, searching for new tumor markers for NPC is still desired and merited.

Therefore, the present invention proposes a new nasopharyngeal carcinoma malignancy biomarker specifically for NPC diagnostic to detect the malignancy of nasopharyngeal carcinoma much more effectively.

SUMMARY OF THE INVENTION

The primary objective of the present invention is to provide a method of detecting the malignancy of nasopharyngeal carcinoma and a nasopharyngeal carcinoma malignancy biomarker, wherein macrophage inflammatory protein 3α (MIP-3α) is used to evaluate the malignancy of nasopharyngeal carcinoma, whereby selecting a correct therapy method and promoting the therapy effect.

To achieve the abovementioned objective, the present invention proposes a method of detecting malignancy of nasopharyngeal carcinoma and a nasopharyngeal cancer malignancy biomarker, which is based on the evidence that immunohistochemical detection of MIP-3α overexpression in NPC cells and secretion of MIP-3α from NPC cell lines; and the evidence that elevated MIP-3α levels in sera from untreated NPC patients from a prospective cohort, compared with controls; and the evidence that close associations of high serum MIP-3α levels with tumor relapse in a retrospective cohort collected over 5 years, wherefore the present invention adopts MIP-3α as a biomarker of nasopharyngeal cancer to predict the malignancy of nasopharyngeal cancer, detect metastasis, or estimate the probability of metastasis.

In the following, the present invention is described in detail in cooperation with the attached drawings to facilitate easily understanding the objective, characteristics and accomplishments of the present invention.

BRIEF DESCRIPTION OF THE DRAWINGS

FIGS. 8(a)~8(c) are diagrams showing time courses of post-treatment levels of MIP-3α, EBV DNA load and EBV VCA IgA in selected NPC patients with locoregional recurrence (N=5); and FIGS. 9(a)~9(c) are diagrams showing time courses of post-treatment levels of MIP-3α, EBV DNA load and EBV VCA IgA in selected NPC patients with distant metastasis (N=5).

DETAILED DESCRIPTION OF THE INVENTION

Macrophage inflammatory protein MIP-3α, encoded by the CCL20 gene, is a CC-chemokine that induces leukocyte migration into inflammation sites and regulates leukocyte trafficking through lymphoid tissues [22]. Increased expression of MIP-3α has been reported in several inflammatory conditions [23-25] and cancers, including breast adenocarcinoma, hepatocellular carcinoma and pancreatic ductal cell adenocarcinoma [26], and this chemokine has also been implicated in promoting growth and migration of pancreatic cancer cells [26, 27].

In the present invention, we adopt MIP-3α as a biomarker of nasopharyngeal carcinoma to accurately and effectively detect the malignancy of nasopharyngeal carcinoma. According to the relative MIP-3α expression level of a specimen of a testee and of at least one specimen of at least one control, we can investigate malignant status of the specimen of the testee. If the MIP-3α expression level of said specimen is overexpressed, the testee is determined to have nasopharyngeal carcinoma; or the testee is determined to have metastasis of nasopharyngeal carcinoma or have high probability of metastasis of nasopharyngeal carcinoma. Also, MIP-3α and EBV DNA load or EBA-VCA IgA are used as a two-marker panel for discriminating primary NPC patient. In the following, the present invention discloses a method of detecting malignancy of nasopharyngeal carcinoma by MIP-3α.

Figure 1:
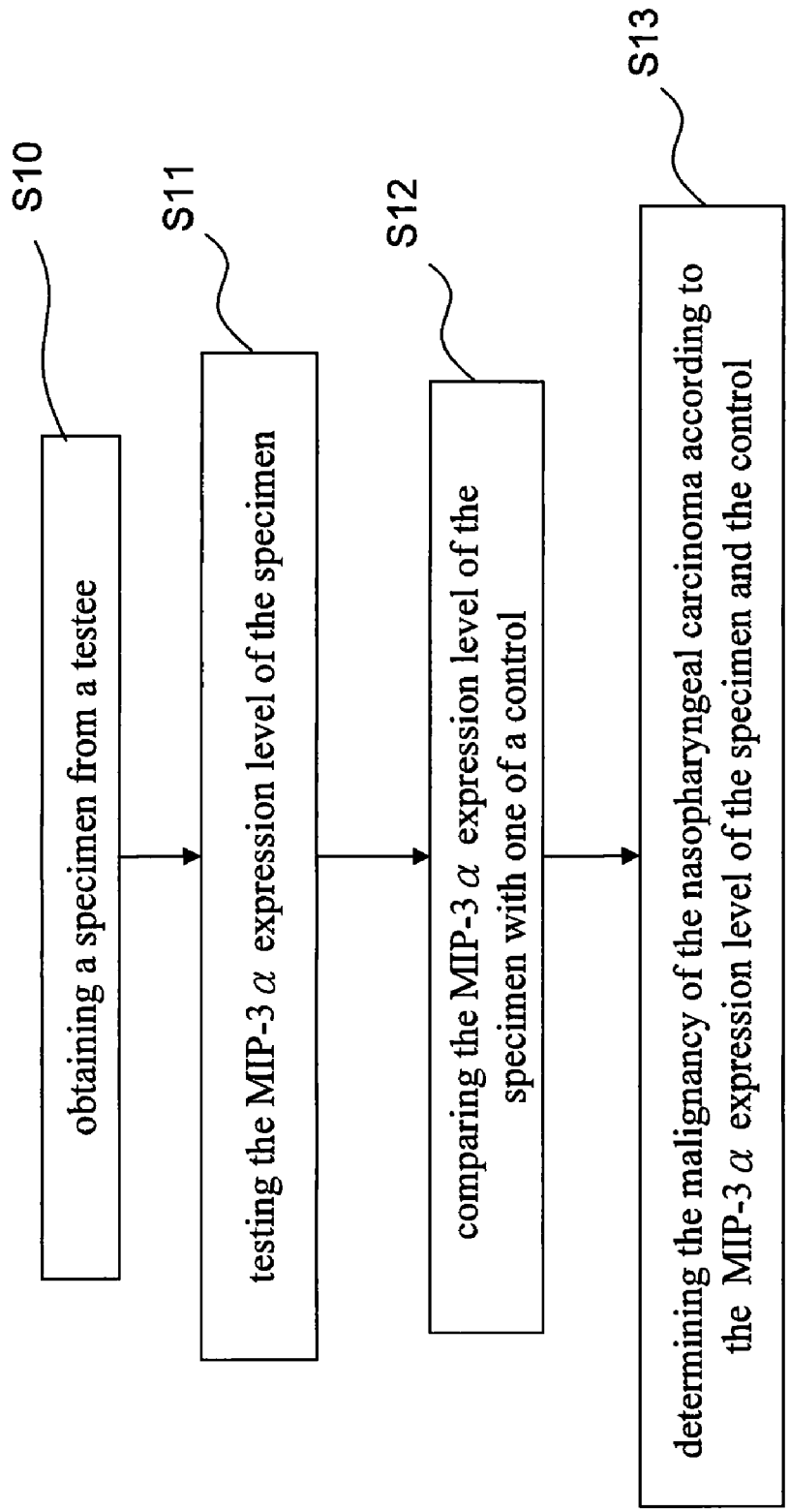
FIG. 1 is a flowchart of the steps of a method for testing the malignancy of nasopharyngeal cancer according to the present invention.

Refer to FIG. 1 for a flowchart of the steps of a method for detecting the malignancy of nasopharyngeal carcinoma according to the present invention. Firstly, as shown in the step of S10, a specimen is obtained from a testee. The specimen could be from a nasopharynx of the testee or it could be a blood sample from the testee. Next, in the step of S11, the specimen is tested quantitatively or semi-quantitatively. We obtain the protein expression level of the specimen, wherein the protein expression level is a MIP-3α expression level. Then, the MIP-3α expression level of the specimen of the testee is compared with the MIP-3α expression level of at least one control that is a normal control, as shown in the step of S12. Alternatively, the control could be selected from a control group consisting of a negative nasopharynex tissue control, a positive nasopharynx tissue control and combinations of negative and positive nasopharynx tissue controls. The control group may be a normal nasopharyngeal tissue or a cancerous nasopharyngeal tissue. Finally, in the step of S13, the malignancy of the nasopharyngeal carcinoma is determined according to the MIP-3α expression level of the specimen and the control.

Moreover, in case that the MIP-3α expression level of the specimen is overexpressed, the testee is determined to have nasopharyngeal carcinoma or the testee is determined to have metastasis of nasopharyngeal carcinoma or have high probability of metastasis of nasopharyngeal carcinoma.

Figure 2:
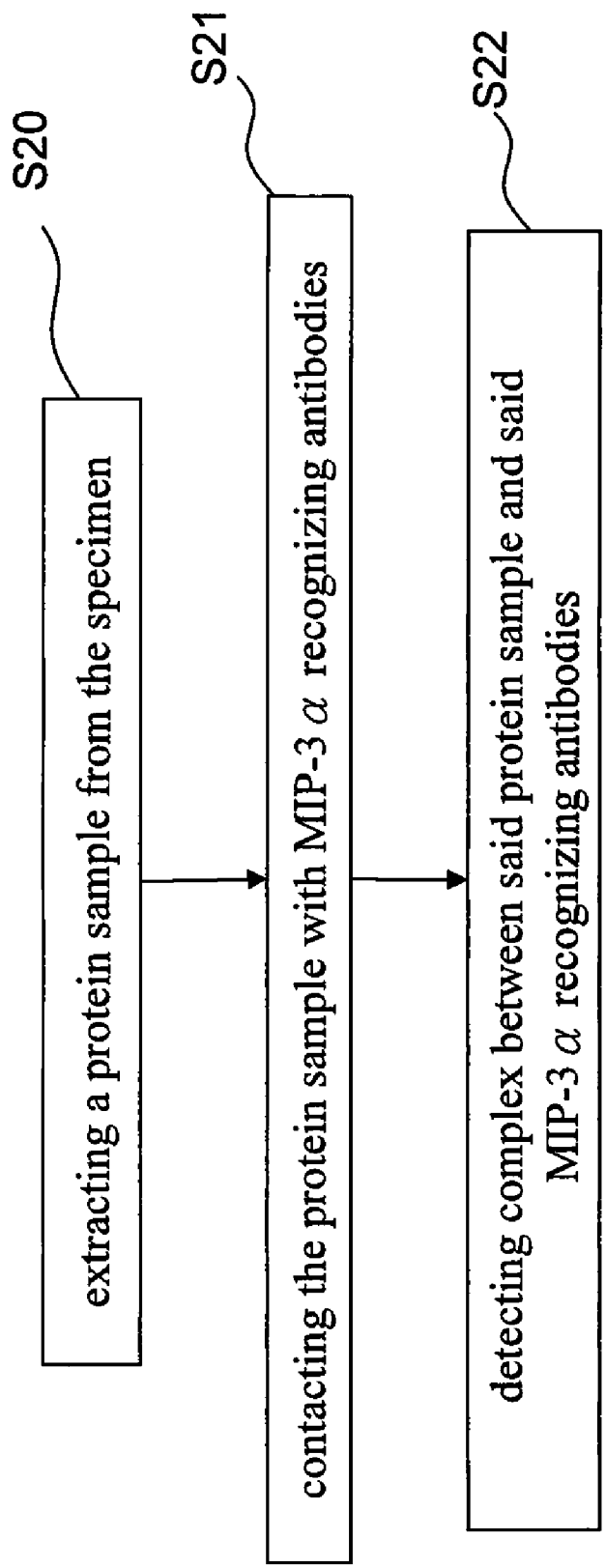
FIG. 2 is a flowchart of the steps of a method for comparing protein expression level of a testee and a control according to the present invention.

Refer to FIG. 2 for a flowchart of the steps of a method for comparing MIP-3α expression level of the specimen of the testee and the control according to the present invention. Firstly, in Step S20, a protein sample is extracted from the specimen. Wherein, total RNA extraction and quantitative real-time PCR are used in one embodiment of the present invention. The experiment condition of the embodiment is shown as follows. Paired tumor and pericancerous normal tissues are homogenized in liquid nitrogen with a pestle and mortar, and incubated at room temperature in 2 ml of RNAzol B reagent (Tel-Test Inc, Friendwood, Tex.). After 5 min, 0.4 ml of chloroform is added, and the mixture is shaken vigorously for 15 sec, incubated at room temperature for another 5 min, and then centrifuged at 12,000 g at 4° C. for 15 min. One ml of the upper colorless aqueous phase is transferred to a new microfuge tube, mixed with 1 ml isopropanol for 10 min for RNA precipitation, and centrifuged at 12,000 g at 4° C. for 15 min. The RNA pellet is washed with 1 ml of 75% ethanol, briefly vacuum dried, and dissolved in RNase-free water. The RNA is further purified using the RNeasy cleanup kit (Qiagen Inc., Valencia, Calif.), according to the manufacturer's protocol. First-strand cDNA is synthesized from 5 µl of total RNA, and then mixed with a reaction mixture consisting of commercially-available primers (MIP-3α Hs01011368_ml and normalization control GAPDH, Hs99999905_ml; Assay-on-Demand, Applied Biosystems, Foster City, Calif.), RNase-free water, and the TaqMan Universal PCR Master Mix. Real-time PCR is performed using the provided protocol and the following PCR conditions: 50° C.×2 min followed by 95° C.×10 min, and then 45 cycles of 95° C.×15 seconds and 60° C.×1 min. The experiments are repeated in triplicate and mean fold-changes were calculated.

Next, in Step S21, the protein sample contacts recognizing antibodies, which can recognize MIP-3α. The recognizing antibodies are monoclonal antibodies or polyclonal antibodies. The protein samples may contact the MIP-3α recognizing antibody with an immunoassay method. The immunoassay method may be the radioimmunoassay method, the Western blot assay method, the immunofluorescent assay, the enzyme immunoassay, the immunoprecipitation method, the chemiluminescent assay method, the immunohistochemical assay method, the dot blot assay method, or the slot blot assay method. Then, in Step S22, the complexes of the protein samples and the MIP-3α recognizing antibody are compared.

In one embodiment of the present invention, immunohistochemical analyses are performed using an automatic immunhistochemistry (IHC) staining device according to the manufacturer's instructions (Bond, Vision Biosystems) by using an anti-MIP-3α antibody (R&D Systems). The immunohistochemical staining and scoring methods are described as follows.

Tissue sections are retrieved using Bond Epitope Retrieval Solution 1 on the Bond-max automated immunostainer (Vision BioSystems, Melbourne, Australia). The tissue sections are treated with liquid DAB reagent (DAKO), with 3,3'-diaminobenzidine tetrahydrochloride used as the chromogen and hematoxylin as the counterstaining reagent. Images of the stained slides are obtained using the ScanScope CT automated slide-scanning system (Aperio Technologies, Vista, Calif.). Expression of MIP-3α is scored using a combined scoring method that accounts for both the staining intensity and the percentage of stained cells [1]. Strong, moderate, weak, and negative staining intensities were scored as 3, 2, 1, and 0, respectively. For each of the intensity scores, the percentage of cells that stained at such level is estimated visually. The resulting combined score is calculated as the sum of the percentage of stained cells multiplied by the intensity scores. For example, a case with 20% weak staining, 30% moderate staining, and 50% strong staining would be assigned a score of 230 (20×1+30×2+50×3=230) out of a possible score of 300. The specimens are independently evaluated by two pathologists without prior knowledge of the clinical data.

Furthermore, Enzyme-linked immunosorbent assay (ELISA) can also be used to detect the presence of an MIP-3α antibody in a sample. For example, NPC-TW02 and -TW04 cell lines (derived from keratinizing and undifferentiated carcinomas, respectively) and the pancreatic carcinoma cell line, Panc-1, are routinely grown in DMEM supplemented with 10% FBS, 100 U/ml penicillin and 100 mg/ml streptomycin (complete medium). For ELISA, these cell lines are cultured at the cell density of $1 \times 10^6$ cells/500 μl complete medium in 24-well culture plates for 24 hours at 37° C. Supernatants (conditioned media) are collected from the wells, centrifuged at 1,500 rpm for 20 min and stored at −80° C. for further experiments.

MIP-3α levels in the tested samples were determined using the ELISA kit Quantikine® for human MIP-3α (R&D Systems Minneapolis, Minn.). Human recombinant MIP-3α (R&D Systems) is used as the standard. Briefly, 100 μl of serum samples or standard is added to microtiter plates coated with a murine monoclonal antibody against human MIP-3α and incubated for 2 h at room temperature. The plates are then washed three times with wash buffer, a horseradish peroxidase-conjugated polyclonal antibody is added to the wells, and the plates are incubated for 2 hr at room temperature. The plates are then washed, and hydrogen peroxide and tetramethylbenzidine are added for color development at room temperature for 30 min. The reaction is stopped by addition of 2 N sulfuric acid, and the color intensity in each well is measured as the optical density using a microplate reader set to 450 nm. A standard curve is constructed by plotting the optical value of the standard and the amounts of MIP-3α in the respective samples. Each experiment is performed in duplicate.

Figure 3:
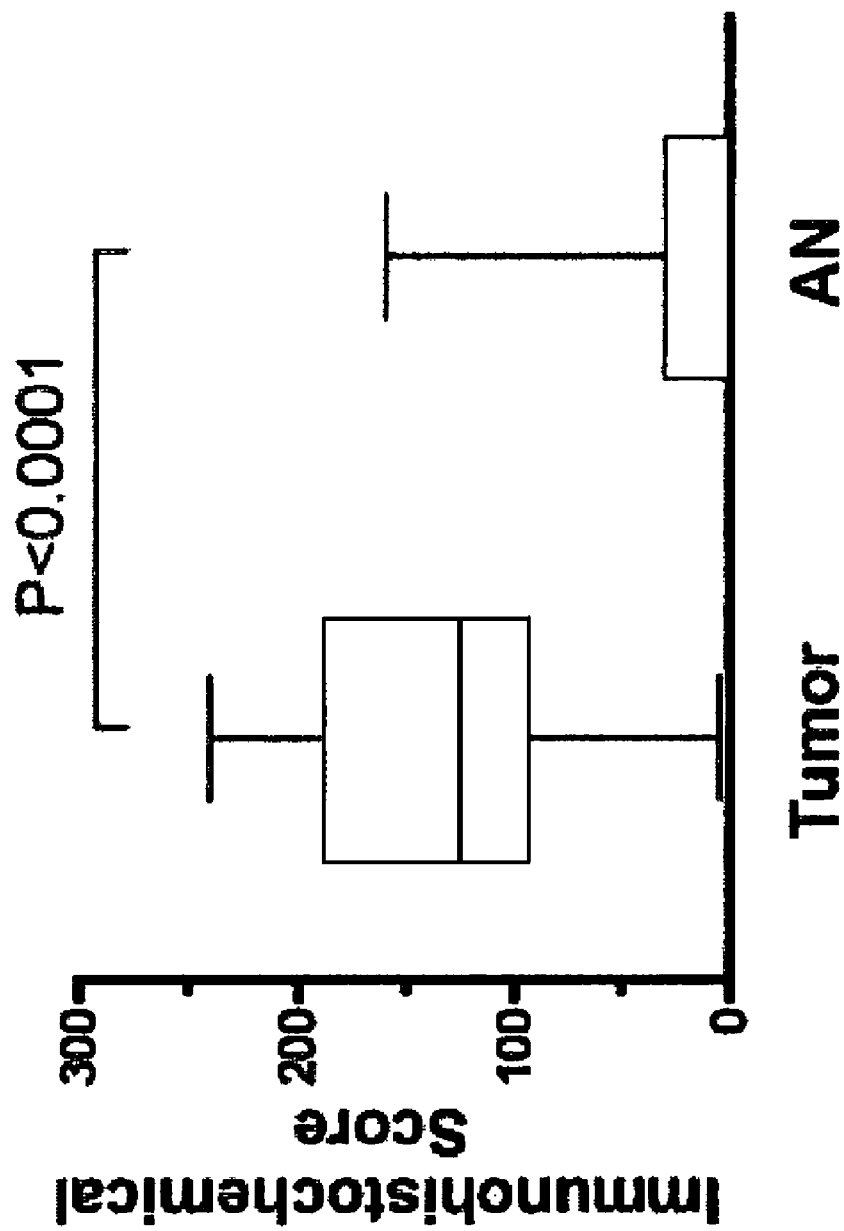
FIG. 3 is a box chart analysis of the immunohistochemical staining scores of MIP-3α in 28 paired AN and tumor tissues.

Refer to FIG. 3 for a box chart analysis of the immunohistochemical staining scores of MIP-3α in 28 paired AN and tumor tissues. The above illustration reveals that MIP-3α expression levels in cells from NPC tissue is significantly higher than those in cells from normal tissue.

Figure 4:
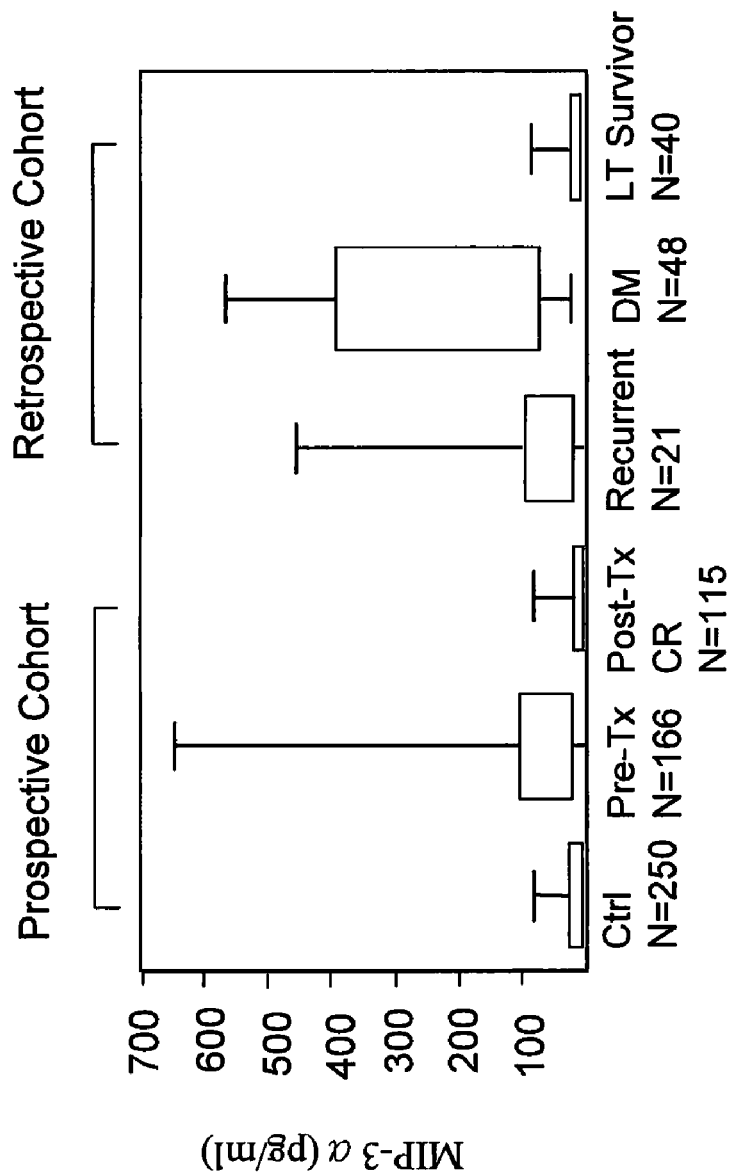
FIG. 4 is a bar chart of association of serum MIP-3α levels with disease status among NPC patients.

The present invention provides the correlation between serum MIP-3α levels and disease status is shown in FIG. 4. The statistical data from testing the serum MIP-3α levels are elevated in NPC patients. In FIG. 4, Ctrl represents controls; pre-Tx represents pre-treatment; post-Tx represents post-treatment; CR represents complete remission 6 months after treatment; Recurrent represents locoregional recurrence; DM represents distant metastasis; LT represents long-term survivors. The serum MIP-3α levels in 166 untreated NPC patients from the prospective cohort is significantly higher than those from 250 controls. The serum MIP-3α levels in 115 post-treatment NPC patients are significantly reduced in FIG. 4. Moreover, the serum MIP-3α levels in patients with CR are lower than those in patients with recurrence or DM. The serum MIP-3α levels in recurrent patients are not statistically different from those in untreated patients. The serum MIP-3α levels in patients showing DM are significantly higher than those in untreated patients and recurrent patients. The serum MIP-3α levels are not statistically different between controls and patients with CR, between controls and long-term survivors, or between patients with CR and long-term survivors. The findings from the cells suggest that serum MIP-3α can be a potential marker for detection of NPC.

In the present invention, it is verified that MIP-3α promotes migration and cell invasion of NPC cells in vitro, corresponding to the above conclusion. Two NPC cell lines, NPC-TW02 and NPC-TW04, are examined for expression and secretion of MIP-3α. The detail of cell migration assay and cell invasion assay is disclosed in the following. Cell migration ability is evaluated using a chemotaxis chamber (Corning Inc., Lowell, Mass.) with a polycarbonate membrane (pore size of 8 μm) placed between the two chambers. Cells ($3 \times 10^5$) in 300 μl of culture medium are applied to the upper chamber, and 600 μl of medium containing the indicated concentrations of MIP-3α and 5 μg/ml of collagen is added to the lower chamber. After the chamber was subjected to a 16-hr incubation at 37° C., the membrane is fixed in methanol for 10 min and stained with hematoxylin and eosin. Cells on the upper surface of the filter are carefully removed with a cotton swab, and the cells that had migrated through the membrane to the lower surface of the filter are counted in 9 different fields under a light microscope. Each migration assay is performed in triplicate determinations from three separate experiments.

The Cell Invasion Assay Kit (Chemicon, Temecula, Calif.) is used to measure the invasive capability of the cancer cell lines. Briefly, the polycarbonate membranes (8 μm pore size) of the upper compartments of the provided Transwell culture chambers are coated with the provided ECMatrix™. Cells ($1 \times 10^5$) are suspended in 100 μl serum-free medium and placed in the upper compartments, and the lower compartments were filled with 500 μl of medium containing 10% FBS and the indicated agents. After the device is subjected to a 48-hr incubation, the membranes are fixed in methanol and stained with hematoxylin and eosin. Cells on the upper surface of each filter were carefully removed with a cotton swab, and the cells that had migrated through the membrane to the lower surface of the filter were counted in 9 different fields under a light microscope.

Knockdown of MIP-3α by RNA interference is the other experiment for an evidence to the contrary, which proves the MIP-3α is related to the malignancy of NPC. The experiment condition is disclosed as follows. The pGSH1-Luciferase shRNA vector is constructed by inserting the luciferase cDNA in place of the GFP cDNA of the GeneSilencer pGSH1-GFP shRNA Vector (Gene Therapy Systems, San Diego, Calif.) backbone, from the Ava I to BsrG I restriction sites. A 22-nucleotide duplex (5'-GGATACACAGACCG-TATTCTTC-3') (SEQ ID NO: 1) is designed for shRNA targeting against MIP-3α (GenBank Accession No. NM_004591) and cloned into the pGSH1-Luciferase shRNA vector to generate pGSH1-Luciferase-sh MIP-3α. NPC-TW04 cells are transfected with the pGSH1-Luciferase or pGSH1-Luciferase-sh MIP-3α☐vectors using Lipofectamine 2000 (Invitrogen, Carlsbad, Calif.). After G418 selection for 3 weeks, two vector control stable clones and two MIP-3α-silenced stable clones are obtained and used for subsequent experiments.

Figure 5A:
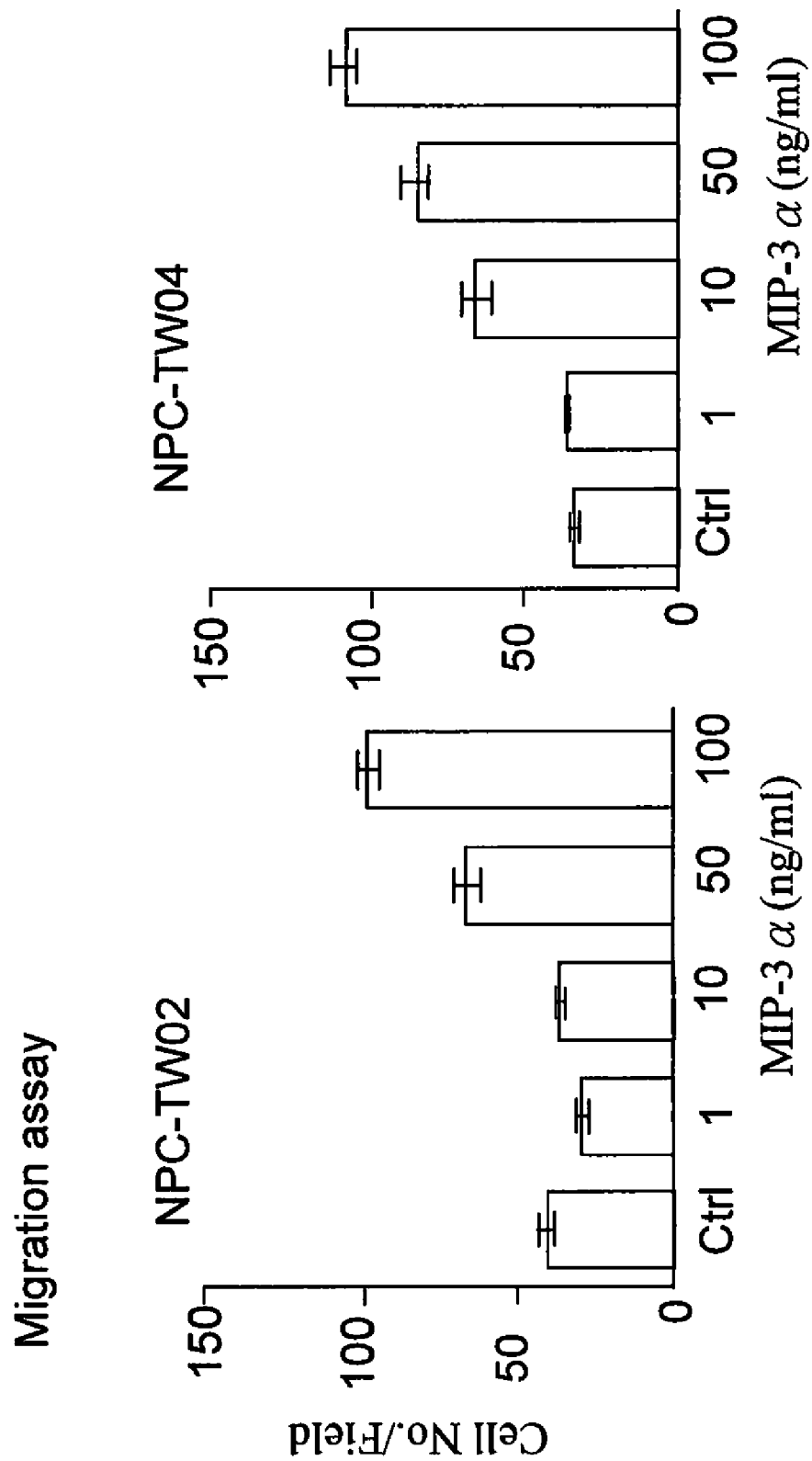
FIGS. 5(a)~5(c) are bar charts of MIP-3α promoting migration and invasion of NPC cells.
Figure 5B:
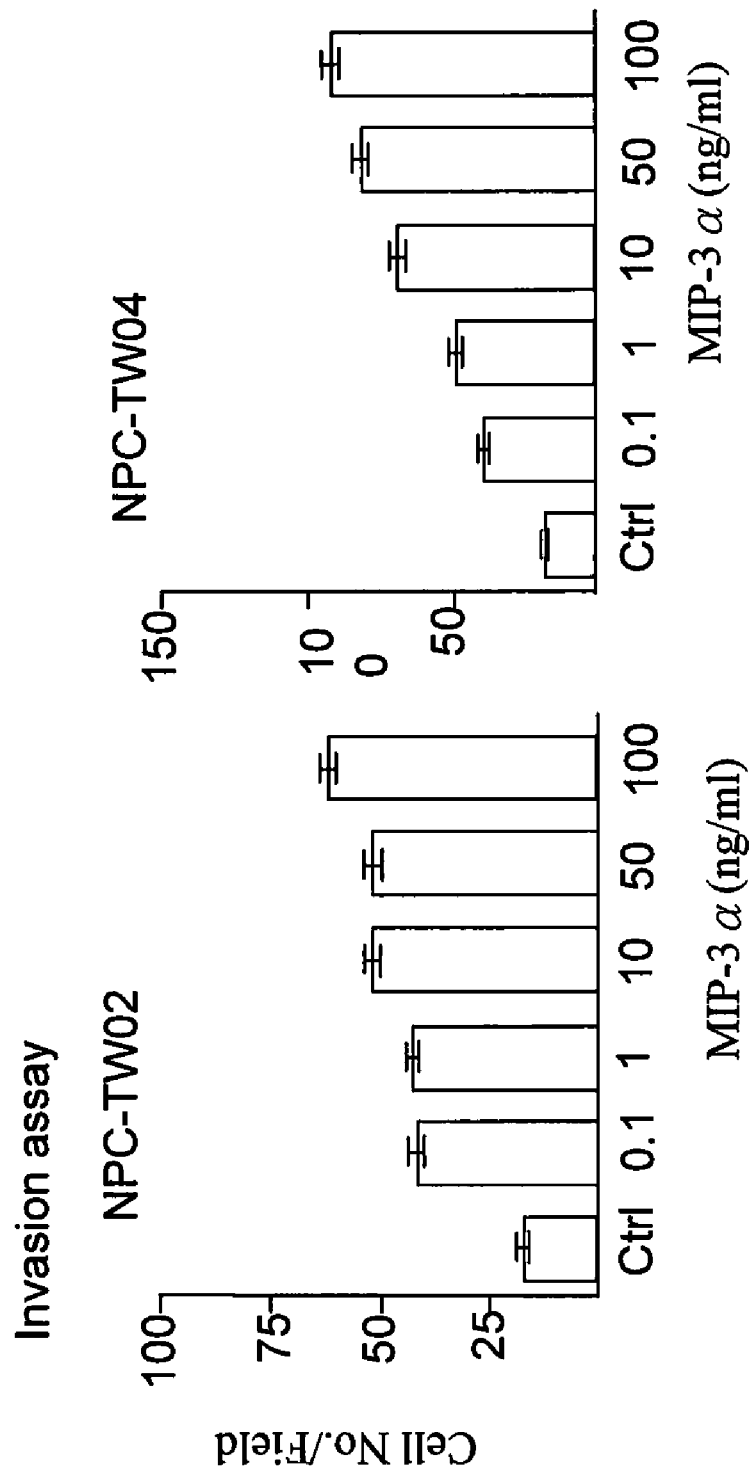
Figure 5C:
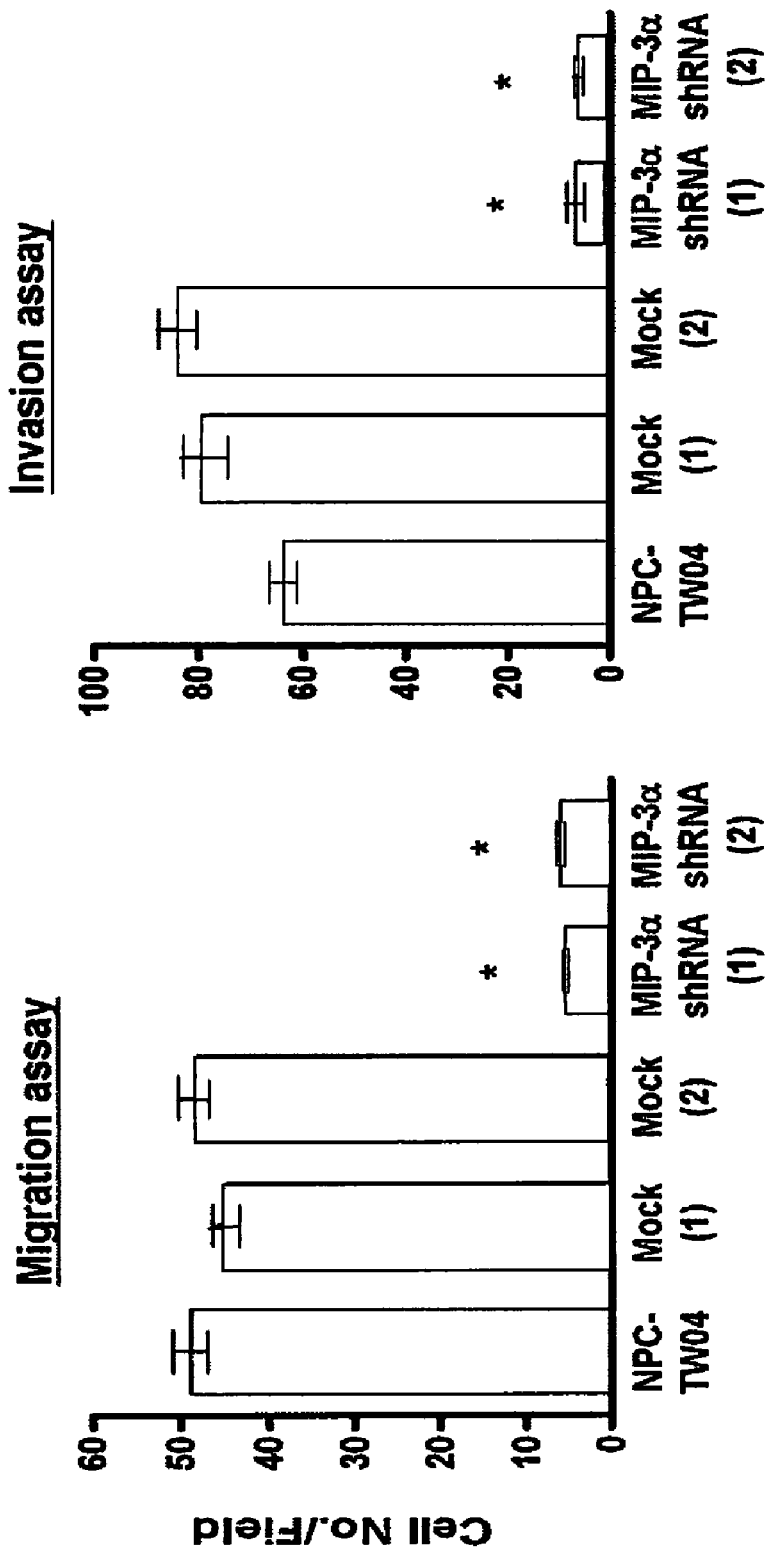

Refer to FIG. 5(*a*), FIG. 5(*b*) and FIG. 5(*c*). FIG. 5(*a*) and FIG. 5(*b*) illustrate migration and invasion assays of NPC-TW02 and NPC-TW04 cells in the presence of various concentrations of MIP-3α, respectively. FIG. 5(*c*) illustrates migration and invasion assays of the parental NPC-TW04 cells, two MIP-3α-silenced clones. These indicate that MIP-3α can mediate the migration and invasion process of NPC cells in vitro.

As mentioned in the prior art, epstein-barr virus DNA load (EBA DNA load) and EBA-viral capsid antigen IgA (EBA VCA IgA) are currently used for NPC diagnosis, but the high false-positive rates are problematic for primary screening in endemic areas. Herein, patient characteristics and serum/plasma levels of MIP-3α, EBV VCA IgA, and EBA DNA load are integrated in Table 1. Comparing with the prior art, analysis of serum/plasma samples from the 116 untreated patients showed that both serum MIP-3α levels and plasma EBV DNA load were significantly elevated in patients with higher T stage, N stage, and overall stage but did not significantly differ with age, gender, or pathologic classification.

TABLE 1

| | No. | MIP-3αLevels (pg/mL) | EBV DNA load (copy number/mL) | EBV VCA IgA Titers (median) |
|---|---|---|---|---|
| Gender | | | | |
| Female | 60 | 99.7 ± 15.7 | 5,962 ± 4,022 | 75.5 ± 22.9(40) |
| Male | 106 | 73.6 ± 7.5 | 7,770 ± 2,753 | 83.7 ± 22.3(40) |
| Age | | | | |
| <48 | 83 | 91.0 ± 12.6 | 5,032 ± 2,967 | 66.6 ± 22.3(40) |
| >48 | 83 | 76.2 ± 8.8 | 7,924 ± 3,458 | 97.7 ± 22.6(80) |
| T stage | | | | |
| T1-T2 | 82 | 61.3 ± 9.7 | 4,959 ± 2,591 | 77.7 ± 22.7(40) |
| T3-T4 | 72 | 101.1 ± 11.2 | 5909 ± 3,223 | 77.9 ± 22.6(40) |
| N stage | | | | |
| 0, 1 | 86 | 61.9 ± 9.5 | 3,419 ± 2,797 | 69.7 ± 22.2(40) |
| 2, 3 | 72 | 102.6 ± 5.5 | 7,733 ± 2,975 | 89.8 ± 23.1(40) |
| Overall stage | | | | |
| I-II | 52 | 46.1 ± 8.9 | 3962 ± 109 | 71.9 ± 23.1(40) |
| III-IV | 106 | 97.3 ± 9.9 | 7,832 ± 3,015 | 81.6 ± 22.3(40) |
| Pathology (WHO lassification) | | | | |
| I | 2 | | | |
| II | 35 | 100.6 ± 21.0 | 14,229 ± 8,808 | 72.5 ± 23.6(40) |
| III | 129 | 79.8 ± 8.0 | 4,475 ± 1,680 | 82.7 ± 22.1(40) |

Figure 6:
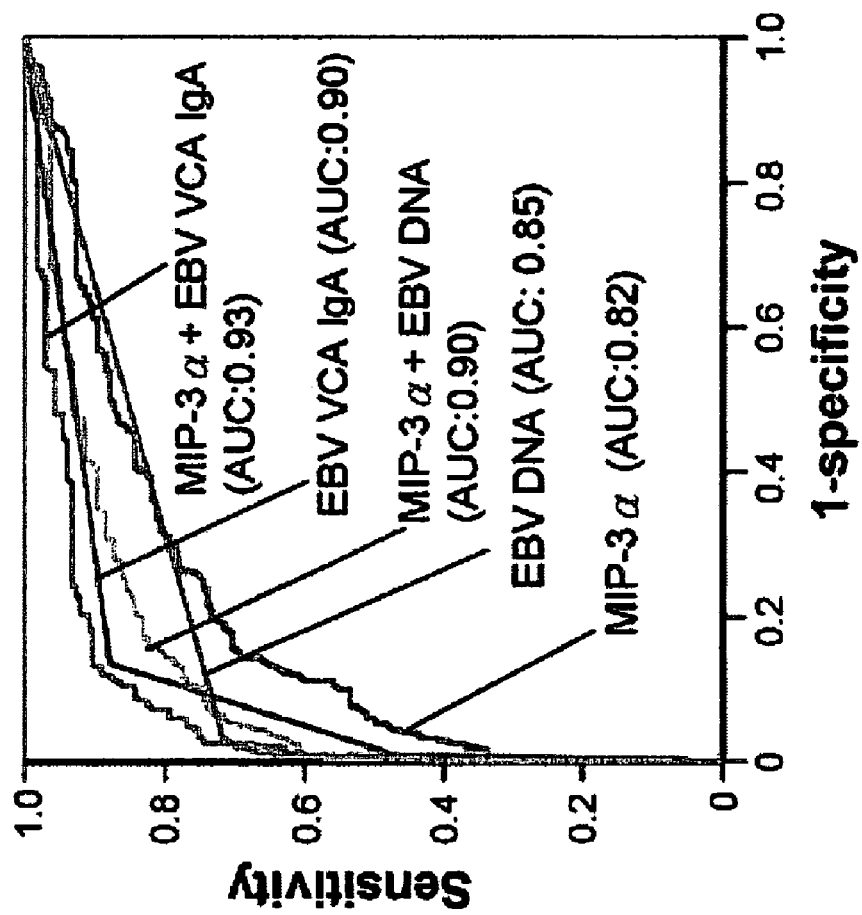
FIG. 6 is a diagram showing diagnosis efficacy of EBV DNA load, EBV VCA IgA titer and MIP-3α level.

Refer to FIG. 6. ROC curve analysis shows that EBV VCA IgA alone (AUC=0.90%; 95% confidence interval, 0.87-0.93) does slightly better than EBV DNA load alone (AUC=0.87-0.93; 95% CI, 0.81-0.89) or MIP-3α alone (AUC=0.82; 95% CI, 0.78-0.86). When the MIP-3α is combined with EBV VCA IgA or EBV DNA in a logistic regression model (28), the screening efficacy of these two-marker panels is better than that of each alone (AUC=0.93; 95% CI, 0.90-0.96 for MIP-3α and EBV VCA IgA and AUC=0.90; 95% CI, 0.86-0.93 for MIP-3α and EBV DNA). Although the 95% CI of the AUC of the two-marker combination overlaps with the AUC of single marker, these results still indicate that addition of MIP-3α levels to the EBV-based screening protocol may improve the efficacy of primary NPC screening.

Figure 7A:
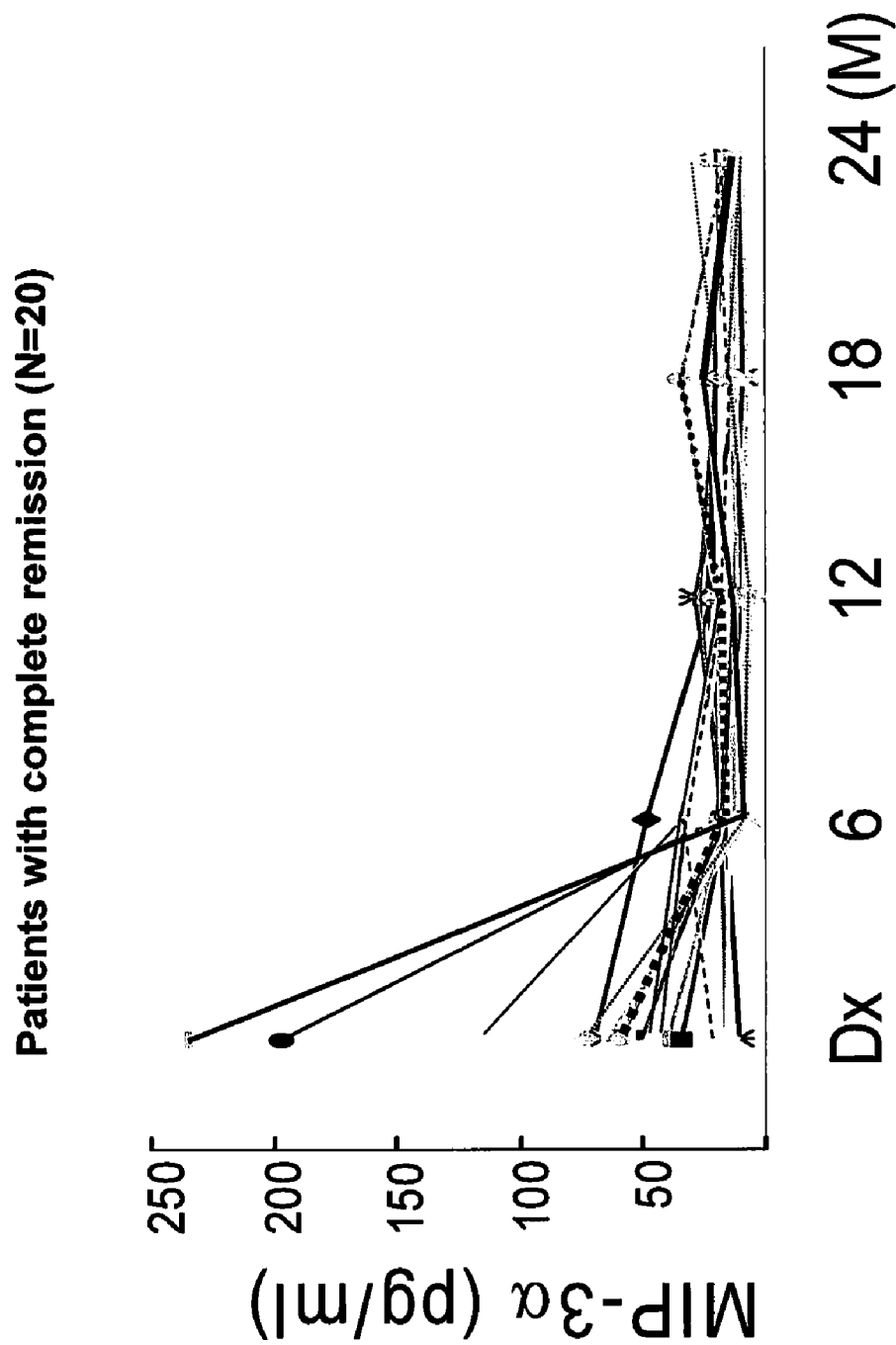
FIGS. 7(a)~7(c) are diagrams showing time courses of post-treatment levels of MIP-3α, EBV DNA load and EBV VCA IgA in selected NPC patients with complete remission (N=20)
Figure 7B:
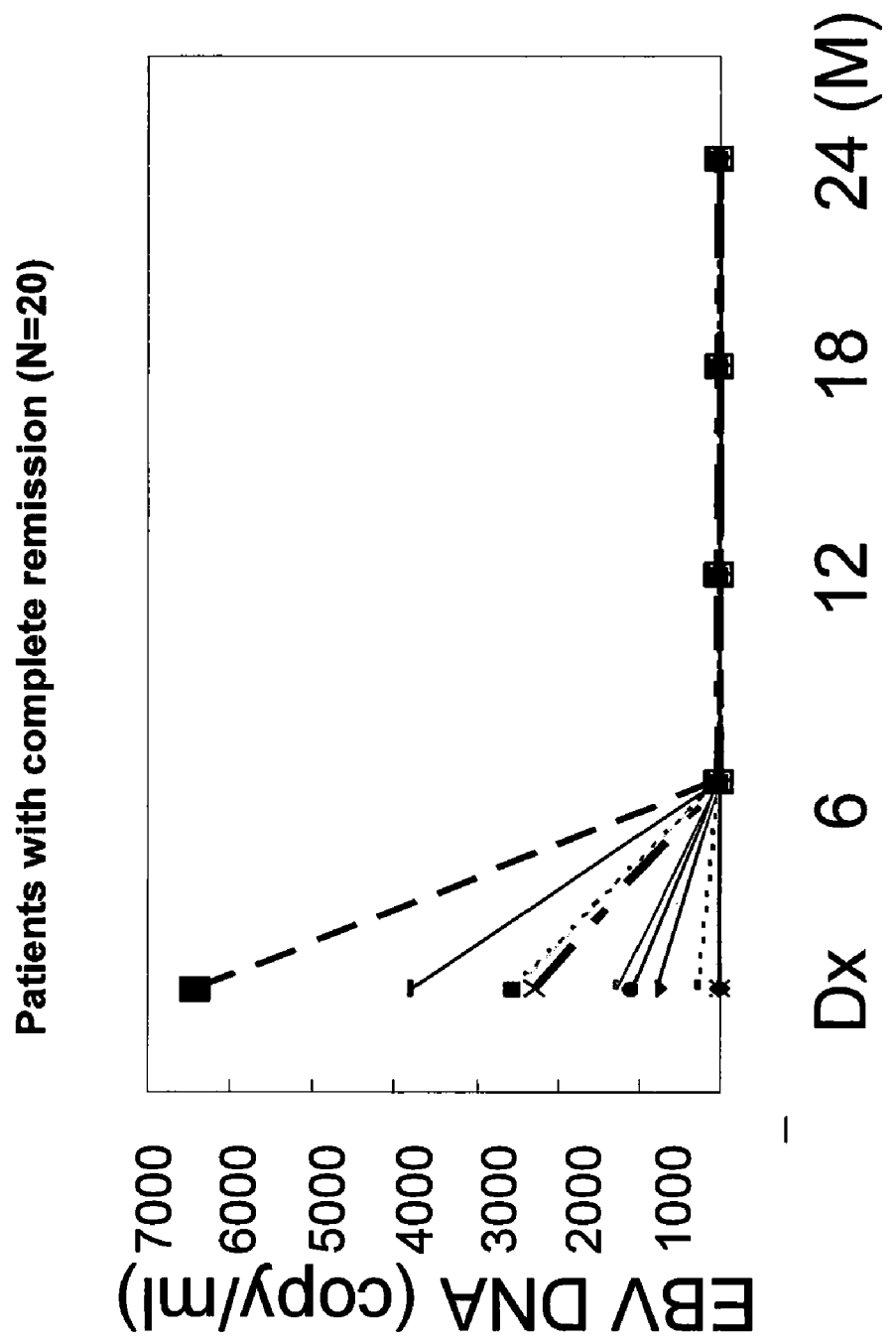
Figure 7C:
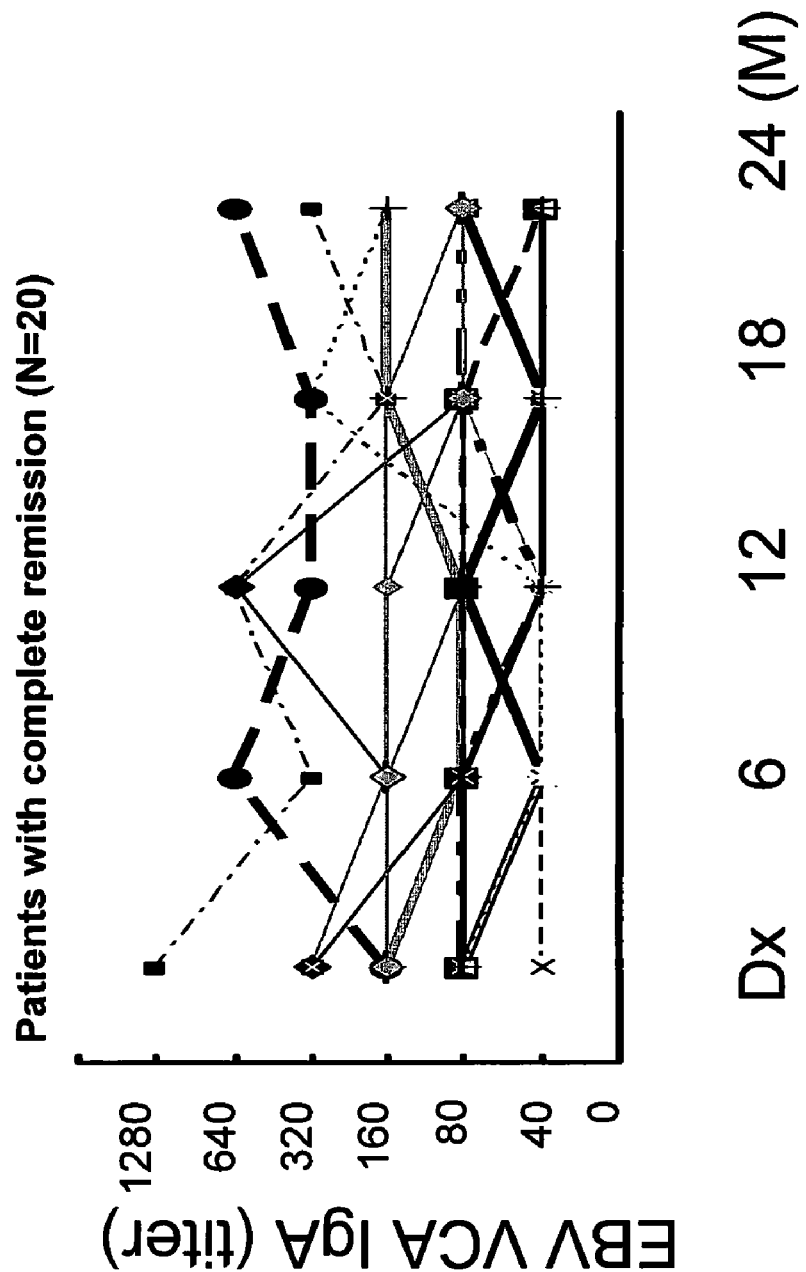
Figure 8B:
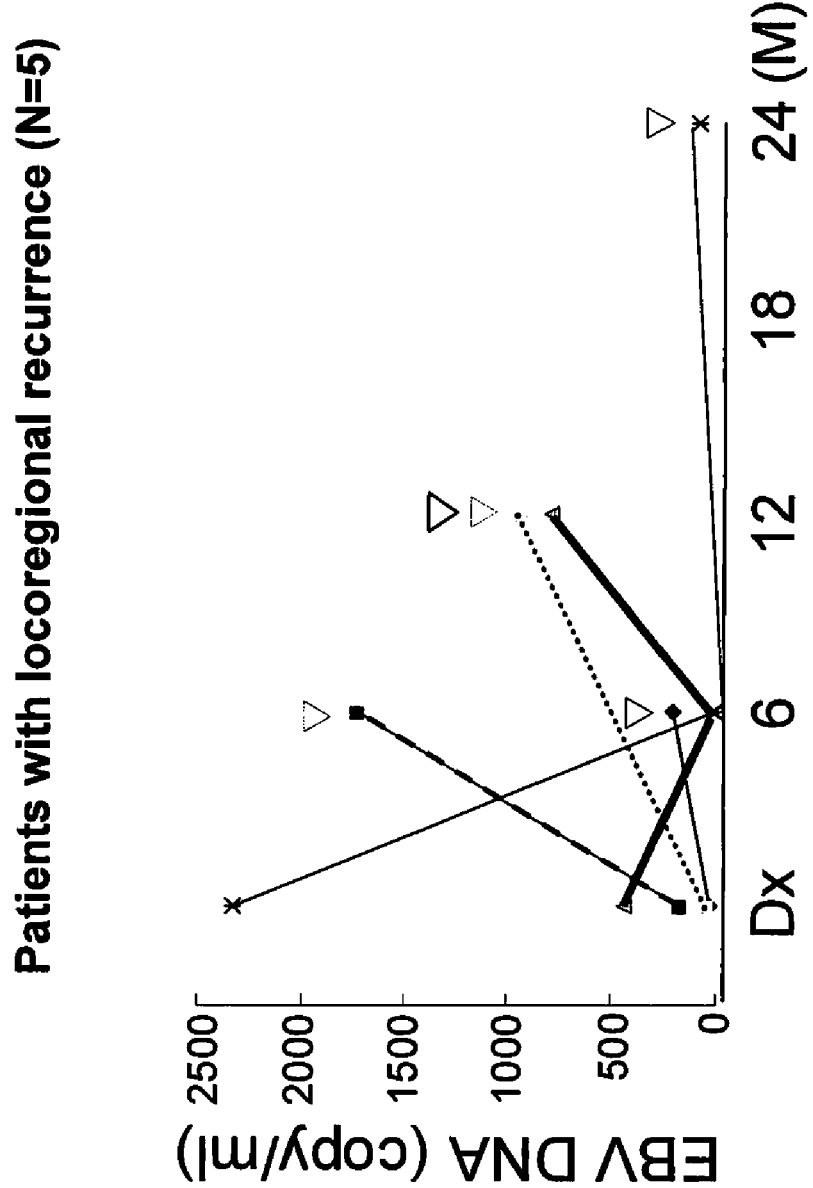
Figure 8C:
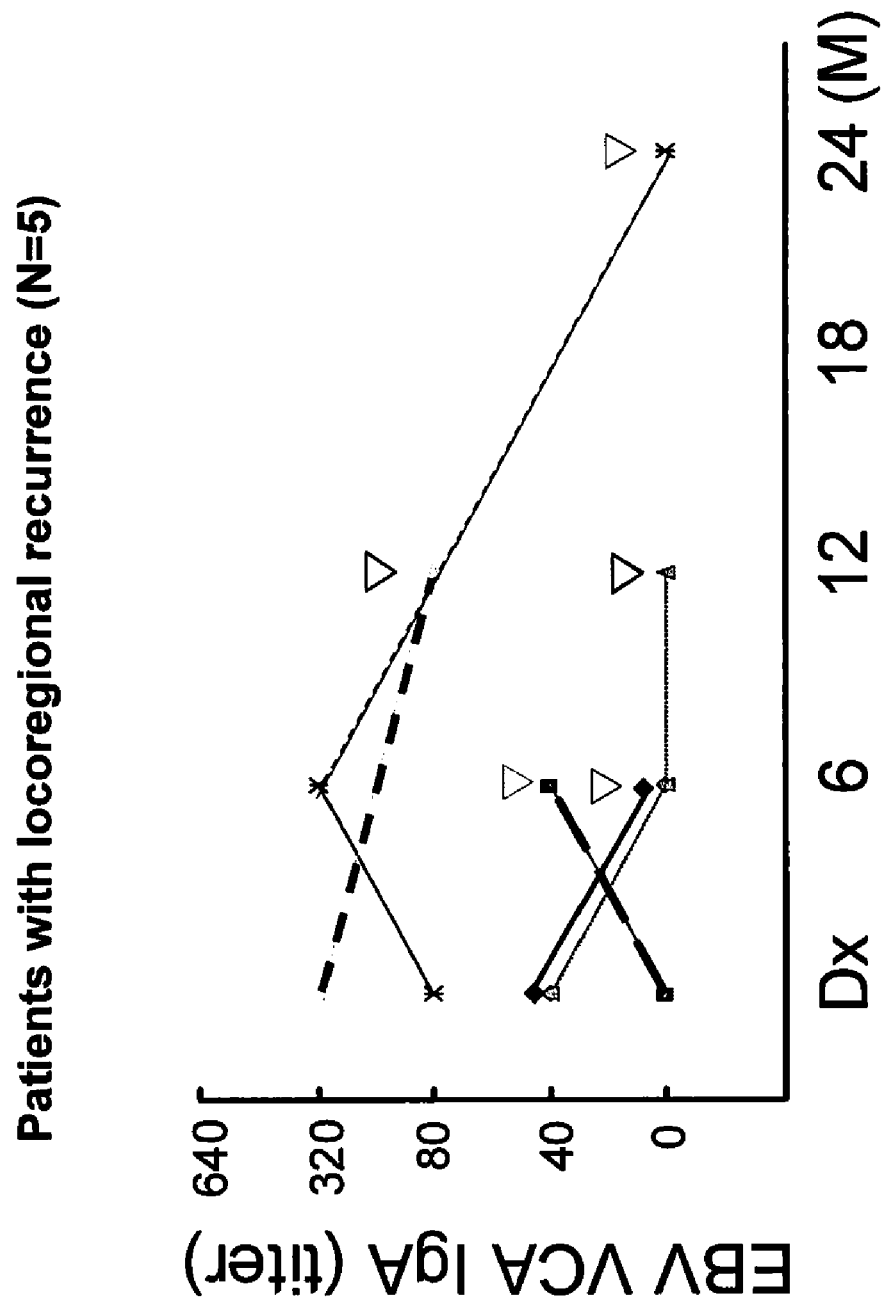

Refer to FIGS. 7(a)~7(c), FIGS. 8(a)~8(c) and FIGS. 9(a)~9(c). The diagrams shows time courses of post-treatment levels of MIP-3α, EBV DNA load and EBV VCA IgA in selected NPC patients with different disease statuses. To explore dynamic changes in the above-described markers in explore dynamic changes in the above-described markers in NPC patients, serial sera/plasma samples of the prospective cohort were investigated pretreatment and every 6 months following treatment for 2 years. In FIGS. 7(a)~7(c), among 20 patients with CR, the MIP-3α levels at 6 and 24 months post-treatment were drastically lower in 18 and 19 patients, respectively compared with the corresponding pretreatment samples. The EBV DNA load decreased to undetectable levels post-treatment in all 20 samples. However, the EBV VCA IgA titers of patients after treatment decreased in only 9 and 10 of these patients. Therefore, MIP-3α may be a potential marker of CR, like EBA DNA load. Further, FIGS. 8(a)~8(c) and FIGS. 9(a)~9(c) disclose serial sera/plasma samples from 5 NPC patients with locoregional recurrence and 5 with post-treatment distant metastasis. Elevated MIP-3α levels and EBV DNA load were detected in 4 of 5 and all 5 recurrent patients, respectively in FIGS. 8(a)~8(c), and in 5 of 5 and 4 of 5 patients with distant metastasis, respectively, in FIGS. 9(a)~9(c). Also, elevated MIP-3α levels was observed in 2 of the 5 patients who developed distant metastasis even before distant metastasis had been clinically confirmed.

Summing up the above, the present invention proposes MIP-3α as a new marker for NPC because MIP-3α is overexpressed in NPC cells and that its serum level is significantly elevated in NPC patients. Also, our study reports that MIP-3α promotes the migration and invasion of two NPC cell lines and that knockdown of endogenously expressed MIP-3α impairs their migration and invasion capabilities. Furthermore, MIP-3α can be used as a useful supplement to EBV VCA IgA, and EBV DNA load for primary screening or post-treatment monitoring of NPC. According to the characteristic of MIP-3α, this new biomarker can play in a crucial role for NPC prognostic and diagnostic.

The present invention has been demonstrated with the embodiments described above. However, they are only to exemplify the present invention but not to limit the scope of the present invention. Any equivalent modification or variation according to the spirit of the present invention is to be also included within the scope of the present invention, which is based on the claims stated below.

REFERENCE

[1] Hsu M M, Lin B L. [Immunologic study on nasopharyngeal carcinoma patients: correlation of mononuclear cell reactivity to phytohemagglutinin and clinical stage]. Taiwan yi xue hui za zhi 1983; 82: 972-6;

[2] Hsu M M, Tu S M. Nasopharyngeal carcinoma in Taiwan. Clinical manifestations and results of therapy. Cancer 1983; 52: 362-8;

[3] Lee A W, Foo W, Law S C, et al. Nasopharyngeal carcinoma: presenting symptoms and duration before diagnosis. Hong Kong medical journal=Xianggang yi xue za zhi/Hong Kong Academy of Medicine 1997; 3: 355-61;

[4] Huang S C, Lui L T, Lynn T C. Nasopharyngeal cancer: study III. A review of 1206 patients treated with combined modalities. International journal of radiation oncology, biology, physics 1985; 11: 1789-93;

[5] Lee A W, Law S C, Foo W, et al. Retrospective analysis of patients with nasopharyngeal carcinoma treated during 1976-1985: survival after local recurrence. International journal of radiation oncology, biology, physics 1993; 26: 773-82;

[6] Sham J S, Cheung Y K, Chan F L, Choy D. Nasopharyngeal carcinoma: pattern of skeletal metastases. The British journal of radiology 1990; 63: 202-5;

[7] Cheng S H, Jian J J, Tsai S Y, et al. Long-term survival of nasopharyngeal carcinoma following concomitant radiotherapy and chemotherapy. Int J Radiat Oncol Biol Phys 2000; 48: 1323-30;

[8] Lin J C, Jan J S, Hsu C Y, Liang W M, Jiang R S, Wang W Y. Phase III study of concurrent chemoradiotherapy versus radiotherapy alone for advanced nasopharyngeal carcinoma: positive effect on overall and progression-free survival. J Clin Oncol 2003; 21: 631-7;

[9] Chang K P, Tsang N M, Chen C Y, Su J L, Hao S P. Endoscopic management of skull base osteoradionecrosis. The Laryngoscope 2000; 110: 1162-5;

[10] Wang C C. Re-irradiation of recurrent nasopharyngeal carcinoma—treatment techniques and results. International journal of radiation oncology, biology, physics 1987; 13: 953-6;

[11] Chang K P, Hao S P, Tsang N M, Ueng S H. Salvage surgery for locally recurrent nasopharyngeal carcinoma-A 10-year experience. Otolaryngol Head Neck Surg 2004; 131: 497-502;

[12] Chang Y S, Tyan Y S, Liu S T, Tsai M S, Pao C C. Detection of Epstein-Barr virus DNA sequences in nasopharyngeal carcinoma cells by enzymatic DNA amplification. J Clin Microbiol 1990; 28: 2398-402;

[13] Raab-Traub N. Epstein-Barr virus and nasopharyngeal carcinoma. Semin Cancer Biol 1992; 3: 297-307;

[14] Wu T C, Mann R B, Epstein J I, et al. Abundant expression of EBER1 small nuclear RNA in nasopharyngeal carcinoma. A morphologically distinctive target for detection of Epstein-Barr virus in formalin-fixed paraffin-embedded carcinoma specimens. Am J Pathol 1991; 138: 1461-9;

[15] Henle G, Henle W. Epstein-Barr virus-specific IgA serum antibodies as an outstanding feature of nasopharyngeal carcinoma. Int J Cancer 1976; 17: 1-7;

[21] Lee A W, Poon Y F, Foo W, et al. Retrospective analysis of 5037 patients with nasopharyngeal carcinoma treated during 1976-1985: overall survival and patterns of failure. Int J Radiat Oncol Biol Phys 1992; 23: 261-70;

[22] Yoshie O, Imai T, Nomiyama H. Chemokines in immunity. Adv Immunol 2001; 78:57-110;

[23] Homey B, eu-Nosjean M C, Wiesenborn A, et al. Up-regulation of macrophage inflammatory protein-3 alpha/CCL20 and CC chemokine receptor 6 in psoriasis. J Immunol 2000; 164: 6621-32;

[24] Matsui T, Akahoshi T, Namai R, et al. Selective recruitment of CCR6-expressing cells by increased production of MIP-3 alpha in rheumatoid arthritis. Clin Exp Immunol 2001; 125: 155-61;

[25] Nakayama T, Fujisawa R, Yamada H, et al. Inducible expression of a CC chemokine liver- and activation-regulated chemokine (LARC)/macrophage inflammatory protein (MIP)-3 alpha/CCL20 by epidermal keratinocytes and its role in atopic dermatitis. Int Immunol 2001; 13: 95-103;

[26] Kleeff J, Kusama T, Rossi D L, et al. Detection and localization of Mip-3alpha/LARC/Exodus, a macrophage proinflammatory chemokine, and its CCR6 receptor in human pancreatic cancer. Int J Cancer 1999; 81: 650-7;

[27] Kimsey T F, Campbell A S, Albo D, Wilson M, Wang T N. Co-localization of macrophage inflammatory protein-3alpha (Mip-3alpha) and its receptor, CCR6, promotes pancreatic cancer cell invasion. Cancer J 2004; 10: 374-80; and

[28] Mor G, Visintin I, Lai Y, et al. Serum protein markers for early detection of ovarian cancer. Proc. Natl Acad Sic USA 2005; 102:7677-82.

SEQUENCE LISTING

<160> NUMBER OF SEQ ID NOS: 1

<210> SEQ ID NO 1
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 1
ggatacacag accgtattct tc                                              22

[16] Ho H C, Ng M H, Kwan H C, Chau J C. Epstein-Barr-virus-specific IgA and IgG serum antibodies in nasopharyngeal carcinoma. Br J Cancer 1976; 34: 655-60;

[17] Fan H, Nicholls J, Chua D, et al. Laboratory markers of tumor burden in nasopharyngeal carcinoma: a comparison of viral load and serologic tests for Epstein-Barr virus. Int J Cancer 2004; 112: 1036-41;

[18] Lin J C, Wang W Y, Chen K Y, et al. Quantification of plasma Epstein-Barr virus DNA in patients with advanced nasopharyngeal carcinoma. N Engl J Med 2004; 350: 2461-70;

[19] Lo Y M, Chan L Y, Lo K W, et al. Quantitative analysis of cell-free Epstein-Barr virus DNA in plasma of patients with nasopharyngeal carcinoma. Cancer Res 1999; 59: 1188-91;

[20] Chang K P, Hao S P, Lin S Y, et al. The 30-bp deletion of Epstein-Barr virus latent membrane protein-1 gene has no effect in nasopharyngeal carcinoma. The Laryngoscope 2006; 116: 541-6;

What is claimed is:

1. A method of detecting malignancy of nasopharyngeal carcinoma, comprising steps:

obtaining a blood specimen from a testee;

quantitatively measuring a macrophage inflammatory protein 3α (MIP-3α) expression level of said blood specimen; and comparing said MIP-3α expression level of said blood specimen with a MIP-3α expression level of at least one control, wherein said control is a healthy subject without nasopharyngeal carcinoma; and detecting a presence level malignancy of nasopharyngeal carcinoma in said testee according to said MIP-3α expression level of said specimen and said control, wherein if the MIP-3α expression level of said specimen is higher than said control, the testee is determined to have nasopharyngeal carcinoma or have probability of metastasis of nasopharyngeal carcinoma.

2. The method of detecting malignancy of nasopharyngeal carcinoma as claimed in claim 1, wherein said step of comparing said MIP-3α expression level of said blood specimen with said MIP-3α expression level of said control includes the following steps:

contacting said blood specimen with at least one antibody has feature of recognizing the MIP-3α to form a protein-antibody complex; and detecting an expression level of said protein-antibody complex.

3. The method of detecting malignancy of nasopharyngeal carcinoma as claimed in claim 2, wherein said antibody is a monoclonal antibodies or a polyclonal antibody.

4. The method of detecting malignancy of nasopharyngeal carcinoma as claimed in claim 2, wherein said step of contacting said blood specimen with at least one antibody has feature of recognizing the MIP-3α to form the protein-antibody complex uses an enzyme-linked immunosorbent assay method or an immunoassay method selected from a group consisting of: a radioimmunoassay method, a Western blot assay method, an immunofluorescent assay, an enzyme immunoassay, an immunoprecipitation method, a chemiluminescent assay method, an immunohistochemical assay method, a dot blot assay method, and a slot blot assay method.

5. The method of detecting malignancy of nasopharyngeal carcinoma as claimed in claim 1, wherein said testee has or had said nasopharygeal carcinoma.

* * * * *